United States Patent
Tanaka

(10) Patent No.: US 10,159,633 B2
(45) Date of Patent: Dec. 25, 2018

(54) HAIR CLEANSING COMPOSITION

(71) Applicant: SHISEIDO COMPANY, LTD., Tokyo (JP)

(72) Inventor: Keita Tanaka, Yokohama (JP)

(73) Assignee: SHISEIDO COMPANY, LTD., Tokyo (JP)

(*) Notice: Subject to any disclaimer, the term of this patent is extended or adjusted under 35 U.S.C. 154(b) by 0 days.

(21) Appl. No.: 15/522,110

(22) PCT Filed: Oct. 30, 2015

(86) PCT No.: PCT/JP2015/080824
§ 371 (c)(1),
(2) Date: Apr. 26, 2017

(87) PCT Pub. No.: WO2016/068328
PCT Pub. Date: May 6, 2016

(65) Prior Publication Data
US 2017/0333327 A1 Nov. 23, 2017

(30) Foreign Application Priority Data

Oct. 31, 2014 (JP) ................. 2014-222139

(51) Int. Cl.
| | | |
|---|---|---|
| C11D 1/22 | (2006.01) |
| A61K 8/60 | (2006.01) |
| A61K 8/44 | (2006.01) |
| A61Q 5/02 | (2006.01) |
| A61K 8/04 | (2006.01) |
| A61K 8/20 | (2006.01) |
| A61K 8/23 | (2006.01) |
| A61K 8/46 | (2006.01) |
| A61K 8/73 | (2006.01) |
| A61K 8/88 | (2006.01) |
| A61K 8/34 | (2006.01) |
| A61K 8/42 | (2006.01) |
| A61K 8/81 | (2006.01) |
| A61K 8/90 | (2006.01) |
| A61K 8/19 | (2006.01) |

(52) U.S. Cl.
CPC ........... *A61K 8/60* (2013.01); *A61K 8/046* (2013.01); *A61K 8/19* (2013.01); *A61K 8/20* (2013.01); *A61K 8/23* (2013.01); *A61K 8/345* (2013.01); *A61K 8/42* (2013.01); *A61K 8/44* (2013.01); *A61K 8/442* (2013.01); *A61K 8/463* (2013.01); *A61K 8/466* (2013.01); *A61K 8/731* (2013.01); *A61K 8/737* (2013.01); *A61K 8/738* (2013.01); *A61K 8/817* (2013.01); *A61K 8/88* (2013.01); *A61K 8/90* (2013.01); *A61Q 5/02* (2013.01); *A61K 2800/262* (2013.01); *A61K 2800/5426* (2013.01); *A61K 2800/596* (2013.01); *A61K 2800/75* (2013.01)

(58) Field of Classification Search
None
See application file for complete search history.

(56) References Cited

U.S. PATENT DOCUMENTS

2015/0275133 A1* 10/2015 Doi .................. A61K 8/466
510/127

FOREIGN PATENT DOCUMENTS

| JP | 8-269493 | 10/1996 |
| JP | 3514376 | 5/2001 |
| JP | 2006-274016 | 10/2006 |
| JP | 2012-207019 | 10/2012 |
| JP | 2014-148492 | 8/2014 |

OTHER PUBLICATIONS

PCT/JP2015/080824, ISR and Written Opinion, dated Dec. 28, 2015, 6 pages—Japanese, pages—English.

* cited by examiner

Primary Examiner — Necholus Ogden, Jr.
(74) Attorney, Agent, or Firm — Andrew F. Young, Esq.; Lackenbach Siegel, LLP

(57) ABSTRACT

The purpose of the present invention to solve the problem is to provide a hair cleansing composition that can provide the feeling in use and a stable appearance.
The hair cleansing composition comprises:
  14 to 35% by mass of a sugar and/or a sugar alcohol;
  5 to 20% by mass of an anionic surfactant, 50% or more of the anionic surfactant being an N-acyl-N-methyl taurate and/or an N-acyl-glutamate;
  5 to 20% by mass of an alkamidopropyl betaine and/or an alkyl betaine;
  0.05 to 1% by mass of a cationic polymer; and
  0.01 to 1.5% by mass of an inorganic salt;
wherein the hair cleansing composition has a viscosity of 800 to 20000 mPa·s.

7 Claims, No Drawings

HAIR CLEANSING COMPOSITION

CROSS REFERENCE TO RELATED APPLICATIONS

This application relates to and claims priority as a § 371 national phase, from PCT/JP2015/080824 filed Oct. 30, 2015, the entire contents of which are incorporated herein by reference. This application claims the priority of Japanese Patent Application No. 2014-222139 filed on Oct. 31, 2014, which is incorporated herein by reference

TECHNICAL FIELD

The present invention relates to a hair cleansing composition, and in particular, relates to improvement of the same to provide more stable appearance.

BACKGROUND ART

Desirable properties for a hair cleansing compositions represented by such as a shampoo are not only providing exceptional good lathering (foaming) and a quality of foam, but also an adequate viscosity facilitating a use thereof when applied on a hand, smoothly running fingers through the hair, a stable appearance thereof, and causing no irritation.

In particular, formulating not only commodity common surfactants but also oily materials or water-soluble polymers is examined whether improves feeling in use, but such additional materials may provide foaming with a negative impact and may further leave turbid (cloudy) and opaque (hazy) appearance thereof.

Conventionally, for example, Patent Literatures 1 and 2 disclose technologies developed to increase thickness applying an association phenomenon due to the surfactant and to control thickening quality by adding sugar alcohol etc.

CITATION DOCUMENTS

Patent Literatures

[PATENT LITERATURE 1] Japanese Patent Kokai Publication No. F108-269493 A
[PATENT LITERATURE 2] Japanese Patent Publication No. 3514376

SUMMARY OF THE INVENTION

Technical Problem

However, even such above-described conventional arts are hard to provide concurrently feeling in use such as an adequate viscosity, lathering (foaming) and smoothly running fingers through the hair, the stable appearance thereof, and low irritation.

The present invention was made in view of the above-described problems in association with the conventional art, and the problem to be solved is whether a hair cleansing composition that can achieve concurrently an adequate viscosity, the exceptional feeling in use, and the stable appearance thereof can be provided or not.

Solution To Problem

It is found that a hair cleansing composition according to the present invention can solve the above problems, wherein a hair cleansing composition comprises:

14 to 35% by mass of sugar and/or a sugar alcohol;
5 to 20% by mass of an anionic surfactant, wherein at least 50% by mass of the anionic surfactant that is an N-acyl-N-methyl taurate or an N-acyl-glutamate, or the mixture thereof;
5 to 20% by mass of an alkamidopropyl betaine or an alkyl betaine, or the mixture thereof;
0.05 to 1% by mass of a cationic polymer; and
0.01 to 1.5% by mass of an inorganic salt;
wherein the hair cleansing composition has a viscosity in a range of 800 to 20000 mPa·s.

It is preferred that the hair cleansing composition comprises a nonionic surfactant, of which a fatty acid residue of 12 to 16 carbon atoms.

In the hair cleansing composition, it is preferred that the mass ratio of the anionic surfactant versus alkamidopropyl betaine is in a range of 4/1 to ¼.

In the hair cleansing composition, it is preferred that the inorganic salt is any inorganic salt selected from the group consisting of sodium chloride, sodium sulfate, ammonium chloride, and magnesium chloride.

Hereinafter, the components of the present invention will be explained in more detail.

[Sugars and Sugar Alcohols]

Examples of sugars and/or sugar alcohols used in the present invention may include monosaccharides having 5 to 6 carbon atoms, such as glucose, fructose, galactose, xylose, mannose, arabinose, ribulose, and ribose; and sugar alcohols such as sorbitol, inositol, mannitol, and maltitol, and, in the present invention, one or more compound(s) may be selected and used among these compounds. Preferred sugars and sugar alcohols may include sorbitol, maltitol, fructose, erythritol, and trehalose, and especially preferred sugars and sugar alcohols may include sorbitol, maltitol, erythritol, and trehalose.

According to the present invention, it is considered that sugars and sugar alcohols affect the association condition of surfactants, and the suitable formulable quantity is in a range of 14 to 35% by mass (% by weight) based on the composition. If the formulation quantity is less than 14% by mass viscosity thereof may not be satisfactory. If the formulation quantity exceeds 35% by mass, turbidity or opacity likely due to the surfactant may become visibly recognizable, and the foaming quality with regard to the feeling in use may be impaired.

[Anionic Surfactants]

Examples of anionic surfactants used in the present invention may include the following surfactants.

Anionic surfactants: (1) linear or branched alkyl benzene sulfonates having an alkyl group having an average of 10 to 16 carbon atoms;
(2) alkyl or alkenyl ether sulfates having a linear or branched alkyl group or alkenyl group having an average of 10 to 20 carbon atoms: wherein an average of 0.5 to 8 moles of ethylene oxide, propylene oxide, or butylene oxide is contained per sulfate molecule; or an average of 0.5 to 8 moles as the mixture of ethylene oxide and propylene oxide, in which the mole ratio of ethylene oxide, and propylene oxide is in the range of 0.1/9.9 to 9.9/0.1, is contained per sulfate molecule; or an average of 0.5 to 8 moles of the mixture of ethylene oxide and butylene oxide, in which the mole ratio of ethylene oxide and butylene oxide is in the range of 0.1/9.9 to 9.9/0.1, is contained per sulfate molecule;
(3) alkyl or alkenyl sulphates having an alkyl group or alkenyl group having of an average of 10 to 20 carbon atoms;

(4) α-olefin sulfonates having an average of 10 to 20 carbon atoms per molecule;

(5) alkane sulfonates having an average 10 to 20 carbon atoms per molecule;

(6) saturated or unsaturated fatty acid salts, having an average 10 to 24 carbon per molecule;

(7) alkyl or alkenyl ether carboxylates having an alkyl group or alkenyl group having an average of 10 to 20 carbon atoms, wherein an average of 0.5 to 8 moles of ethylene oxide, propylene oxide, or butylene oxide per molecule, or an average of 0.5 to 8 moles of the mixture of ethylene oxide and propylene oxide per molecule, having the mole ratio of 0.1/9.9 to 9.9/0.1, is added thereon;

(8) α-sulfofatty acid salts or esters thereof having an alkyl group or alkenyl group having an average 10 to 20 carbon atoms;

(9) N-acyl-amino acid-type surfactants having an acyl group having 8 to 24 carbon atoms and a free carboxylic acid residue;

(10) phosphoric acid-type or diester-type surfactants having an alkyl group or alkenyl group having 8 to 24 carbon atoms;

(11) alkyl or alkenyl amide ether sulfates having an alkyl group or alkenyl group of an average of 10 to 20 carbon atoms and an amide bond per molecule, wherein an average of 0.5 to 8 moles of ethylene oxide, propylene oxide, or butylene oxide per molecule, or an average of 0.5 to 8 moles of the mixture of ethylene oxide and propylene oxide per molecule, having the mole ratio range of 0.1/9.9 to 9.9/0.1, is added thereon;

(12) alkyl or alkenyl ether carboxylates having an alkyl group or alkenyl group having an average of 8 to 20 carbon atoms and a hydroxyl ether bond per molecule.

At least one of N-acyl-N-methyl taurate and N-acyl-glutamate is mandatory as an anionic surfactant according to the present invention.

According to the present invention, the formulation amount of the anionic surfactant in the composition is in a range of 5 to 20% by mass and preferably 5 to 15% by mass; the percentage of N-acyl-N-methyl taurate, N-acyl-glutamate or the mixture thereof in the anionic surfactant is preferably 50% by mass or higher, and especially preferably 70% by mass or higher. If the formulation amount of the anionic surfactant in the composition is less than 5% by mass, not only a problem may be caused in the cleansing property but also a thickening effect due to aggregation of surfactants cannot be satisfactorily obtained. If the percentage of N-acyl-N-methyl taurate or N-acyl-glutamate in the anionic surfactant is less than 50% by mass, not only the feeling in use during rinsing may be lost but also low irritant property may be lessened.

In addition, if the formulation quantity of the anionic surfactant in the composition exceeds 20% by mass, not only low irritant property may be lessened, but also the appearance thereof may become turbid and opaque.

[Alkamidopropyl Betaines and Alkyl Betaines]

In the present invention, examples of alkamidopropyl betaines or alkyl betaines may include cocamidepropyl betaine, lauramidepropyl betaine, palm kernelamidepropyl betaine, and lauryl betaine, and particularly lauryl dimethylaminoacetic acid betaine is preferable.

The formulation amount of alkamidopropyl betaine in the composition is 5 to 20% by mass and preferably 5 to 15% by mass. If the formulation amount is less than 5% by mass, thickening cannot satisfactorily be provided; if the formulation amount is 20% by mass or higher, not only low irritant property is lessened, but also the appearance thereof may become turbid or opaque.

[Cationic Polymers]

As cationic polymer suitably used in the present invention, cationic guar gum, cationic cellulose, cationic locust bean gum, polyquaternium-7 (quaternary ammonium salt copolymer obtained from acrylamide and dimethylammonium chloride), etc. can be listed. Specifically, guar hydroxypropyltrimonium chloride as the cationic guar gum, polyquaternium-10 (O-[2-hydroxy-3-(trimethylammonio)propyl]hydroxyethylcellulose chloride) as the cationic cellulose, (O-[2-hydroxy-3-(trimethylammonio)propyl] chloride locust bean gum as the cationic locust bean gum can be listed. The cationic polymer contributes to the improvement of the feeling in use of the hair cleansing composition, and a significant effect can be obtained with 0.05 to 1% by mass thereof in the composition, and preferably with 0.3 to 1% by mass thereof.

[Inorganic Salts]

Furthermore, in the present invention, sodium chloride, sodium sulfate, magnesium chloride, ammonium chloride, etc. are preferably used as the inorganic salt; and they contribute to the aggregate formation of the above-described surfactants and the functional achievement of the cationic polymers. The formulation amount of the inorganic salt is 0.01 to 1.5% by mass in the composition, and preferably 0.01 to 1% by mass.

In the present invention, it is considered that anionic surfactants and alkamidopropyl betaines contribute to excellently increase a thickening property and improve the feeling in use based on the formation of aggregates, as described above, and the formulation ratio is preferably in a range of 4/1 to 1/4, and more preferably 1/1.5 to 1.5/1.

In the present invention, it is preferred to further contain a nonionic surfactant having a fatty acid residue having 12 to 16 carbon atoms for enhancing stable appearance.

Examples of the nonionic surfactants preferably used in the present invention may include propylene glycol laurate, diethylene glycol laurate, cocamide DEA cocamide MEA, glyceryl laurate, diglyceryl laurate, and glyceryl oleate.

The hair cleansing composition obtained in such way can provide a good feeling in use; a clear and transparent appearance thereof; the preferable viscosity in a range of 800 to 20000 mPa·s; and especially preferable in a range of 1000 to 4000 mPa·s so as to ease the usability on the hand.

In the cleansing composition of the present invention, in addition to the above-described essential components, nonionic surfactants other than those described above and commodity components used in such a composition, for example, moisturizers such as propylene glycol and glycerin; viscosity modifiers such as higher alcohols, hydroxymethylcellulose, hydroxyethylcellulose, hydroxypropylcellulose, and methylcellulose; besides, perfumes, colorants. UV absorbers, antioxidants, anti-dandruff agents, bactericides, preservatives, etc. can be formulated as needed.

Effect of the Invention

As explained above, according to the hair cleansing composition of the present invention, the hair cleansing composition of the present invention is less skin irritant and the appearance thereof is not opaque or cloudy (turbid) while keeping the excellent feeling in use, by comprising sugar and/or sugar alcohol, anionic surfactant mandatorily comprising N-acyl-N-methyl taurate and/or N-acyl-glutamate, and alkamidopropyl betaine and/or alkyl betaine.

MODES

Hereinafter, preferred examples of the present invention will be explained.

In the following examples, the formulation amount is in % by mass unless otherwise specified.

At first, evaluation methods as for the following examples will be explained. Appearance: Visual observation with naked eyes:

(A) Transparent or (D) Cloudy or forming precipitation (turbid);

Viscosity (mPa·s): Instrumental measurement using B-type viscometer at 30° C.;

Foaming (lathering): Sensory evaluation when actually used;

Smooth shampooing and smooth rinsing: Using the Combing Test (Techno Hashimoto Co., Ltd.).

Measure each integrated stress values (ISV) of shampooing-combing followed by rinsing-combing and each measurement is repeated 10 times; using the same bleached hairs. The first 3 measurements are excluded. The average value of the rest measurements, i.e., 7 times, is calculated. Each effect on shampooing and rinsing is evaluated based on the following criteria.

Smooth shampooing (Scored from (A) better to (D) worth): (A): ISV is less than 130N; (B): ISV is not less than 130N but less than 150N; (C): ISV is not less than 150N but less than 170N; and (D): ISV is 170N or higher.

Smooth rinsing (Scored from (A) better to (D) worth): (A): ISV is less than 230N; (B): ISV is not less than 230N, but less than 280N; (C): not less than 280N, but less than 330N; and (D): ISV is 330N or higher.

At first, the present inventor carried out the selection or anionic surfactants and amphoteric surfactants.

The results are shown in the following Tables 1 and 2.

TABLE 1

| | Test Examples | | | | | | | |
|---|---|---|---|---|---|---|---|---|
| | 1-1 | 1-2 | 1-3 | 1-4 | 1-5 | 1-6 | 1-7 | 1-8 |
| Water | 60.3 | 59.8 | 60.3 | 64.3 | 60.3 | 60.3 | 60.3 | 59.8 |
| Sugar · Sugar alcohol | | | | | | | | |
| Maltitol | 0 | 0 | 0 | 0 | 0 | 21 | 21 | 21 |
| Sorbitol | 21 | 21 | 21 | 21 | 21 | 0 | 0 | 0 |
| Anionic surfactant | | | | | | | | |
| Sodium N-cocoyl-methyl taurate | 9 | 0 | 0 | 0 | 6 | 9 | 0 | 0 |
| Pottassium N-cocoyl-L-glutamate | 0 | 6 | 0 | 0 | 3 | 0 | 9 | 6 |
| Sodium N-cocoyl glycinate | 0 | 0 | 9 | 5 | 0 | 0 | 0 | 0 |
| Amphoteric surfactant | | | | | | | | |
| Cocamidopropyl betaine | 8 | 9 | 6 | 6 | 6 | 6 | 6 | 9 |
| Cationic polymer | | | | | | | | |
| Polyquaternium-10 (Cationic cellulose) | 0.15 | 0.15 | 0.15 | 0.15 | 0.15 | 0.15 | 0.15 | 0.15 |
| Cationic guar gum | 0.15 | 0.15 | 0.15 | 0.15 | 0.15 | 0.15 | 0.15 | 0.15 |
| Nonionic surfactant | | | | | | | | |
| Propylene glycol laurate | 1 | 1 | 1 | 1 | 1 | 1 | 1 | 1 |
| Inorganic salt | | | | | | | | |
| Sodium chloride | 1 | 1.5 | 1 | 1 | 1 | 1 | 1 | 1.5 |
| Others | | | | | | | | |
| Citric acid | 0.45 | 0.45 | 0.45 | 0.45 | 0.45 | 0.45 | 0.45 | 0.45 |
| Sodium benzoate | q.s. | q.s. | q.s. | q.s. | q.s. | q.s. | q.s. | q.s. |
| Phenoxyethanol | q.s. | q.s. | q.s. | q.s. | q.s. | q.s. | q.s. | q.s. |
| EDTA-2Na | q.s. | q.s. | q.s. | q.s. | q.s. | q.s. | q.s. | q.s. |
| Perfume | q.s. | q.s. | q.s. | q.s. | q.s. | q.s. | q.s. | q.s. |
| Appearance | A | A | D | D | A | A | A | A |
| Viscosity | 4420 | 910 | 2130 | 1730 | 920 | 8240 | 920 | 2450 |
| Lathering | A | B | C | D | B | A | B | B |
| Smooth shampooing | B | B | B | C | B | A | B | B |
| Smooth rinsing | A | A | A | C | B | B | A | A |

TABLE 2

| | Test Examples | | | | | |
|---|---|---|---|---|---|---|
| | 1-1 | 2-1 | 2-2 | 2-3 | 2-4 | 2-5 |
| Water | 60.3 | 60.3 | 60.3 | 58.8 | 56.2 | 58.2 |
| Sugar + Sugar alcohol | | | | | | |
| Sorbitol | 21 | 21 | 21 | 14 | 21 | 21 |
| Anionic surfactant | | | | | | |
| Sodium N-cocoyl-methyl taurate | 9 | 6 | 9 | 15 | 5 | 9 |
| Sodium N-cocoyl glycinate | 0 | 3 | 0 | 0 | 0 | 0 |
| Amphoteric surfactant | | | | | | |
| Lauryl betaine | 0 | 6 | 0 | 0 | 0 | 0 |
| Sodium cocoamphoacetate | 0 | 0 | 6 | 0 | 0 | 0 |
| Cocamidopropyl betaine | 6 | 0 | 0 | 9 | 15 | 9 |
| Cationic polymer | | | | | | |

TABLE 2-continued

| | Test Examples | | | | | |
|---|---|---|---|---|---|---|
| | 1-1 | 2-1 | 2-2 | 2-3 | 2-4 | 2-5 |
| Polyquaternium-10 (Cationic cellulose) | 0.15 | 0.15 | 0.15 | 0.15 | 0.15 | 0.15 |
| Cationic guar gum | 0.15 | 0.15 | 0.15 | 0.15 | 0.15 | 0.15 |
| Nonionic surfactant | | | | | | |
| Propylene glycol laurate | 1 | 1 | 1 | 1 | 1 | 1 |
| Inorganic salt | | | | | | |
| Sodium chloride | 1 | 1 | 1 | 0.5 | 0.1 | 0.1 |
| Others | | | | | | |
| Citric acid | 0.45 | 0.45 | 0.45 | 0.45 | 0.45 | 0.45 |
| Sodium benzoate | q.s. | q.s. | q.s. | q.s. | q.s. | q.s. |
| Phenoxyethanol | q.s. | q.s. | q.s | q.s. | q.s. | q.s. |
| EDTA-2Na | q.s. | q.s. | q.s. | q.s. | q.s. | q.s. |
| Perfume | q.s. | q.s. | q.s. | q.s. | q.s. | q.s. |
| Appearance | A | A | D opaque precipitation | A | A | A |
| Viscosity | 4420 | 2440 | 440 | 1870 | 11000 | 8650 |
| Lathering | B | A | — | A | B | B |
| Smooth shampooing | B | B | — | B | B | B |
| Smooth rinsing | A | C | — | B | A | A |

Referring to the above Table 1 and Table 2, it is remarkable that when Sodium N-cocoyl-methyl taurate (Test Example 1-1) or N-cocoyl glutamate (Test Example 1-2), as the anionic surfactant, and cocamidopropyl betaine, as the amphoteric surfactant, are formulated, the respective evaluation results can satisfy each expected criterion. However, when Sodium N-cocoyl glycinate (1-3 and 1-4) is used, the appearance turns cloudy despite applying an amino acid-based anionic surfactant. When sodium cocoamphoacetate (2-3) is used as the amphoteric surfactant, precipitates appear. When lauryl betaine is used as the amphoteric surfactant (2-1), the smooth rinsing drops slightly, but it is enough from practical use standpoints.

Thus, it is understandable that it is necessary to formulate N-acyl-N-methyl taurate (Sodium N-cocoyl-methyl taurate) or N-acyl-glutamate (N-cocoyl glutamate) as the anionic surfactant and alkamidopropyl betaine (cocamidopropyl betaine) or alkyl betaine (lauryl betaine) as the cationic surfactant.

Subsequently, the present inventor investigated sugars/sugar alcohols. The results are shown in Table 3.

TABLE 3

| | Test Examples | | | | | | |
|---|---|---|---|---|---|---|---|
| | 1-1 | 3-1 | 3-2 | 3-3 | 3-4 | 3-5 | 3-6 |
| Water | 60.3 | 60.3 | 60.3 | 60.3 | 60.3 | 60.3 | 66.3 |
| Sugar · Sugar alcohol | | | | | | | |
| Sorbitol | 21 | 0 | 0 | 0 | 0 | 0 | 0 |
| Maltitol | 0 | 21 | 0 | 0 | 0 | 0 | 0 |
| Fructose | 0 | 0 | 21 | 0 | 0 | 0 | 0 |
| Erythritol | 0 | 0 | 0 | 21 | 0 | 0 | 0 |
| Trehalose | 0 | 0 | 0 | 0 | 21 | 0 | 0 |
| Hydroxypropyl cyclodextrin | 0 | 0 | 0 | 0 | 0 | 21 | 0 |
| Stearyl dihydroxypropyldimonium oligosaccharide | 0 | 0 | 0 | 0 | 0 | 0 | 15 |
| Anionic surfactant | | | | | | | |
| Sodium N-cocoyl-methyl taurate | 9 | 9 | 9 | 9 | 9 | 9 | 9 |
| Amphoteric surfactant | | | | | | | |
| Cocamidopropyl betaine | 6 | 6 | 6 | 6 | 6 | 6 | 6 |
| Cationic polymer | | | | | | | |
| Polyquaternium-10 (Cationic cellulose) | 0.15 | 0.15 | 0.15 | 0.15 | 0.15 | 0.15 | 0.15 |
| Cationic quer gum | 0.15 | 0.15 | 0.15 | 0.15 | 0.15 | 0.15 | 0.15 |
| Nonionic surfactant | | | | | | | |
| Propylene glycol laurate | 1 | 1 | 1 | 1 | 1 | 1 | 1 |
| Inorganic salt | | | | | | | |
| Sodium chloride | 1 | 1 | 1 | 1 | 1 | 1 | 1 |
| Others | | | | | | | |
| Citric acid | 0.45 | 0.45 | 0.45 | 0.45 | 0.45 | 0.45 | 0.45 |
| Sodium benzoate | q.s. | q.s. | q.s. | q.s. | q.s. | q.s. | q.s. |
| Phenoxyethanol | q.s. | q.s. | q.s. | q.s. | q.s. | q.s. | q.s. |
| EDTA-2Na | q.s. | q.s. | q.s. | q.s. | q.s. | q.s. | q.s. |
| Perfume | q.s. | q.s. | q.s | q.s. | q.s. | q.s. | q.s. |
| Appearance | A | A | A | A | A | D | D opaque precipitation |
| Viscosity | 4420 | 8240 | 1760 | 1340 | 5130 | 180 | 1170 |
| Lathering | A | A | B | A | B | — | — |

TABLE 3-continued

|  | Test Examples | | | | | |
|---|---|---|---|---|---|---|
|  | 1-1 | 3-1 | 3-2 | 3-3 | 3-4 | 3-5 | 3-6 |
| Smooth shampooing | B | A | A | A | A | — | — |
| Smooth rinsing | A | B | B | A | A | — | — |

Referring to the above Table 3, it is clear that sorbitol (1-1), maltitol (3-1) and erythritol (3-3) as the sugar/sugar alcohol bring in outstanding characteristics therefore, and fructose (3-2) and trehalose (3-4) bring in also sufficiently satisfactory results.

However, the evaluation results are not satisfactory when either the highly modified/altered hydroxypropyl cyclodextrin (3-5) or stearyl dihydroxypropyldimonium oligosaccharide (3-6) is applied.

Furthermore, the present inventor examined the formulation amount of sugar alcohols.

The results are shown in the following Tables 4-1 and 4-2.

TABLE 4-1

|  | Test Examples | | | | | | |
|---|---|---|---|---|---|---|---|
|  | 4-1 | 4-2 | 4-3 | 1-1 | 4-4 | 4-5 | 4-6 |
| Water | 81.3 | 74.3 | 67.3 | 60.3 | 53.3 | 46.3 | 39.3 |
| Sugar · Sugar alcohol | | | | | | | |
| Sorbitol | 0 | 7 | 14 | 21 | 28 | 35 | 42 |
| Anionic surfactant | | | | | | | |
| Sodium N-cocoyl-methyl taurate | 9 | 9 | 9 | 9 | 9 | 9 | 9 |
| Amphoteric surfactant | | | | | | | |
| Cocamidopropyl betaine | 6 | 6 | 6 | 6 | 6 | 6 | 6 |
| Cationic polymer | | | | | | | |
| Polyquaternium-10 (Cationic cellulose) | 0.15 | 0.15 | 0.15 | 0.15 | 0.15 | 0.15 | 0.15 |
| Cationic guar gum | 0.15 | 0.15 | 0.15 | 0.15 | 0.15 | 0.15 | 0.15 |
| Nonionic surfactant | | | | | | | |
| Propylene glycol laurate | 1 | 1 | 1 | 1 | 1 | 1 | 1 |
| Inorganic salt | | | | | | | |
| Sodium chloride | 1 | 1 | 1 | 1 | 1 | 1 | 1 |
| Others | | | | | | | |
| Citric acid | 0.45 | 0.45 | 0.45 | 0.45 | 0.45 | 0.45 | 0.45 |
| Sodium benzoate | q.s. | q.s. | q.s. | q.s. | q.s. | q.s | q.s. |
| Phenoxyethanol | q.s. | q.s. | q.s. | q.s. | q.s. | q.s. | q.s. |
| EDTA-2Na | q.s. | q.s. | q.s. | q.s. | q.s. | q.s. | q.s. |
| Perfume | q.s. | q.s. | q.s. | q.s. | q.s. | q.s. | q.s. |
| Appearance | A | A | A | A | A | A | A |
| Viscosity | 220 | 490 | 1000 | 4420 | 8250 | 14350 | 11000 |
| Lathering | A | A | A | A | A | B | C |
| Smooth shampooing | A | C | B | B | B | B | B |
| Smooth rinsing | D | A | A | A | B | A | A |

TABLE 4-2

|  | Test Examples | | | | | | |
|---|---|---|---|---|---|---|---|
|  | 4-7 | 4-8 | 4-9 | 4-10 | 4-11 | 4-12 | 4-13 |
| Water | 81.3 | 74.3 | 67.3 | 60.3 | 53.3 | 46.3 | 39.3 |
| Sugar · Sugar alcohol | | | | | | | |
| Maltitol | 0 | 7 | 14 | 21 | 28 | 35 | 42 |
| Anionic surfactant | | | | | | | |
| Sodium N-cocoyl-methyl taurate | 9 | 9 | 9 | 9 | 9 | 9 | 9 |
| Amphoteric surfactant | | | | | | | |
| Cocamidopropyl betaine | 6 | 6 | 6 | 6 | 6 | 6 | 6 |
| Cationic polymer | | | | | | | |
| Cationic guar gum | 0.3 | 0.3 | 0.3 | 0.3 | 0.3 | 0.3 | 0.3 |
| Nonionic surfactant | | | | | | | |
| Propylene glycol laurate | 1 | 1 | 1 | 1 | 1 | 1 | 1 |
| Inorganic salt | | | | | | | |

TABLE 4-2-continued

|  | Test Examples | | | | | | |
|---|---|---|---|---|---|---|---|
|  | 4-7 | 4-8 | 4-9 | 4-10 | 4-11 | 4-12 | 4-13 |
| Sodium chloride | 1 | 1 | 1 | 1 | 1 | 1 | 1 |
| Others |  |  |  |  |  |  |  |
| Citric acid | 0.45 | 0.45 | 0.45 | 0.45 | 0.45 | 0.45 | 0.45 |
| Sodium benzoate | q.s. | q.s. | q.s. | q.s. | q.s. | q.s. | q.s. |
| Phenoxyethanol | q.s. | q.s. | q.s. | q.s. | q.s. | q.s. | q.s. |
| EDTA-2Na | q.s. | q.s. | q.s | q.s. | q.s. | q.s. | q.s. |
| Perfume | q.s. | q.s. | q.s. | q.s. | q.s. | q.s. | q.s. |
| Appearance | A | A | A | A | A | A | A |
| Viscosity | 420 | 750 | 2520 | 6890 | 14740 | 8420 | 3440 |
| Lathering | A | A | A | A | A | B | C |
| Smooth shampooing | A | C | B | B | B | B | B |
| Smooth rinsing | D | B | A | A | B | B | B |

Referring to the above Tables 4-1 and 4-2, the behaviors due to sorbitol and maltitol are similar each other, and results therefrom are good when the formulation amount thereof is in a range of 14% by mass (Test Examples 4-3 and 4-9) to 35% by mass (Test Examples 4-5 and 4-12).

Furthermore, the present inventor examined inorganic salts.

The results are shown in Tables 5 and 6.

TABLE 5

| Test Examples | 5-1 | 5-2 | 5-3 | 5-4 |
|---|---|---|---|---|
| Water | 64.2 | 63.3 | 62.8 | 62.3 |
| Sugar · Sugar alcohol |  |  |  |  |
| Sorbitol | 21 | 21 | 21 | 21 |
| Anionic surfactant |  |  |  |  |
| Sodium N-cocoyl-methyl taurate | 6 | 6 | 6 | 6 |
| Amphoteric surfactant |  |  |  |  |
| Cocamidopropyl betaine | 6 | 6 | 6 | 6 |
| Cationic polymer |  |  |  |  |
| Polyquaternium-10 (Cationic cellulose) | 0.15 | 0.15 | 0.15 | 0.15 |
| Cationic guar gum | 0.15 | 0.15 | 0.15 | 0.15 |
| Nonionic surfactant |  |  |  |  |
| Propylene glycol laurate | 1 | 1 | 1 | 1 |
| Inorganic salt |  |  |  |  |
| Sodium chloride | 0.1 | 1 | 1.5 | 1.7 |
| Others |  |  |  |  |
| Citric acid | 0.45 | 0.45 | 0.45 | 0.45 |
| Sodium benzoate | q.s. | q.s. | q.s. | q.s. |
| Phenoxyethanol | q.s. | q.s. | q.s. | q.s. |
| EDTA-2Na | q.s. | q.s. | q.s. | q.s. |
| Perfume | q.s. | q.s. | q.s. | q.s. |
| Appearance | A | A | A | D |
| Viscosity | 810 | 1540 | 2950 | 3910 |
| Lathering | B | B | B | — |
| Smooth shampooing | A | A | A | — |
| Smooth rinsing | A | A | A | — |

TABLE 6

| Test Examples | 6-1 | 6-2 | 6-3 | 6-4 |
|---|---|---|---|---|
| Water | 63.3 | 63.3 | 63.3 | 64.2 |
| Sugar · Sugar alcohol |  |  |  |  |
| Sorbitol | 21 | 21 | 21 | 0 |
| Maltitol | 0 | 0 | 0 | 21 |
| Anionic surfactant |  |  |  |  |
| Sodium N-cocoyl-methyl taurate | 6 | 6 | 6 | 6 |
| Amphoteric surfactant |  |  |  |  |
| Cocamidopropyl betaine | 6 | 6 | 6 | 6 |
| Cationic polymer |  |  |  |  |
| Polyquaternium-10 (Cationic cellulose) | 0.15 | 0.15 | 0.15 | 0.15 |
| Cationic guar gum | 0.15 | 0.15 | 0.15 | 0.15 |
| Nonionic surfactant |  |  |  |  |
| Propylene glycol laurate | 1 | 1 | 1 | 1 |
| Inorganic salt |  |  |  |  |
| Sodium chloride | 0 | 0 | 0 | 0.1 |
| Sodium sulfate | 1 | 0 | 0 | 0 |
| Magnesium chloride | 0 | 1 | 0 | 0 |
| Ammonium chloride | 0 | 0 | 1 | 0 |
| Others |  |  |  |  |
| Citric acid | 0.45 | 0.45 | 0.45 | 0.45 |
| Sodium benzoate | q.s. | q.s. | q.s. | q.s. |
| Phenoxyethanol | q.s. | q.s. | q.s. | q.s. |
| EDTA-2Na | q.s. | q.s. | q.s. | q.s. |
| Perfume | q.s. | q.s. | q.s. | q.s. |
| Appearance | A | A | A | A |
| Viscosity | 1670 | 3410 | 2450 | 970 |
| Lathering | B | B | B | B |
| Smooth shampooing | A | A | A | A |
| Smooth rinsing | A | A | A | A |

Referring to the above Table 5, even when the formulation amount of inorganic salt is 0.1% by mass (5-1), results are good, but when the formulation amount thereof is reached to 13% by mass (5-4), the appearance is damaged. Thus, the upper limit of the formulation amount of inorganic salt is about 1.5% by mass.

Referring to Table 6, it is understandable that sodium sulfate, magnesium chloride, and ammonium chloride as well as sodium chloride can provide the similar effect.

In addition, the present inventor examined nonionic surfactants. The results are shown in Table 7.

TABLE 7

| Test Examples | 1-1 | 7-1 | 7-2 | 7-3 | 7-4 |
|---|---|---|---|---|---|
| Water | 60.3 | 60.3 | 60.1 | 58.3 | 60.5 |
| Sugar · Sugar alcohol |  |  |  |  |  |
| Sorbitol | 21 | 21 | 21 | 21 | 21 |
| Anionic surfactant |  |  |  |  |  |
| Sodium N-cocoyl-methyl taurate | 9 | 9 | 9 | 9 | 9 |
| Amphoteric surfactant |  |  |  |  |  |
| Cocamidopropyl betaine | 6 | 6 | 6 | 6 | 6 |
| Cationic polymer |  |  |  |  |  |
| Polyquaternium-10 (Cationic cellulose) | 0.15 | 0.3 | 0.3 | 0.3 | 0.3 |
| Cationic guar gum | 0.15 | 0 | 0 | 0 | 0 |
| Nonionic surfactant |  |  |  |  |  |
| Propylene glycol laurate | 1 | 1 | 0 | 0 | 0 |
| Diethylene glycol laurate | 0 | 0 | 1.2 | 0 | 0.3 |
| Cocamido DEA | 0 | 0 | 0 | 3 | 0 |
| Cocamido MEA | 0 | 0 | 0 | 0 | 0.5 |
| Inorganic salt |  |  |  |  |  |

TABLE 7-continued

| Test Examples | 1-1 | 7-1 | 7-2 | 7-3 | 7-4 |
|---|---|---|---|---|---|
| Sodium chloride | 1 | 1 | 1 | 1 | 1 |
| Others | | | | | |
| Citric acid | 0.45 | 0.45 | 0.45 | 0.45 | 0.45 |
| Sodium benzoate | q.s. | q.s. | q.s. | q.s. | q.s. |
| Phenoxyethanol | q.s. | q.s. | q.s. | q.s. | q.s. |
| EDTA-2Na | q.s. | q.s. | q.s. | q.s. | q.s. |
| Perfume | q.s. | q.s. | q.s. | q.s. | q.s. |
| Appearance | A | A | A | A | A |
| Viscosity | 4420 | 1460 | 1020 | 2800 | 1050 |
| Lathering | B | B | B | A | A |
| Smooth shampooing | B | A | B | A | A |
| Smooth rinsing | A | A | A | A | A |

Referring to Table 7, it is understandable that the nonionic surfactant having the fatty acid residue having 12 to 16 carbon atoms can excellently improve usability thereof.

Furthermore, the present inventors examined the kinds of cationized polymers and the formulation amount thereof.

The results are shown in Table 8.

TABLE 8

| Test Examples | 8-1 | 8-2 | 8-3 |
|---|---|---|---|
| Water | 60.2 | 60.5 | 59.6 |
| Sugar · Sugar alcohol | | | |
| Sorbitol | 21 | 21 | 21 |
| Anionic surfactant | | | |
| Sodium N-cocoyl-methyl taurate | 9 | 9 | 9 |
| Amphoteric surfactant | | | |
| Cocamidopropyl betaine | 6 | 6 | 6 |
| Cationic polymer | | | |
| Cationic guar gum | 0.2 | 0.1 | 1 |
| Polyquaternium-10 (Cationic cellulose) | 0.1 | 0 | 0 |
| Polyquaternium-7 (methyl acrylate/dialkyldimethylammonium chloride copolymer) | 0.1 | 0 | 0 |
| Nonionic surfactant | | | |
| Propylene glycol laurate | 1 | 1 | 1 |
| Inorganic salt | | | |
| Sodium chloride | 1 | 1 | 1 |
| Others | | | |
| Citric acid | 0.45 | 0.45 | 0.45 |
| Sodium benzoate | q.s. | q.s. | q.s. |
| Phenoxyethanol | q.s. | q.s. | q.s. |
| EDTA-2Na | q.s. | q.s. | q.s. |
| Perfume | q.s. | q.s. | q.s. |
| Appearance | A | A | A |
| Viscosity | 2520 | 1520 | 3400 |
| Lathering | A | B | A |
| Smoothn shampooing | A | B | A |
| Smooth rinsing | B | B | A |

Referring to the above Table 8, it is clear that not only cationic guar gum and cationic cellulose, of which natural polysaccharides are cationized, but also synthetic cationic polymers, such as methyl acrylate/dialkyldimethylammonium chloride copolymer, are applicable and useful, and the formulation amount in a range of 0.05 to 1% by mass, preferably 0.3 to 1% by mass, can provide preferable results.

[Blending Examples]

| Test Examples | Formulation example 1 | Formulation example 2 | Formulation example 3 | Formulation example 4 | Formulation example 5 |
|---|---|---|---|---|---|
| Water | to 100 | to 100 | to 100 | to 100 | to 100 |
| Sugar · Sugar alcohol | | | | | |
| Sorbitol | 14 | 21 | 10 | 21 | 14 |
| Maltitol | 7 | 0 | 10 | 0 | 7 |
| Anionic surfactant | | | | | |
| Sodium N-cocoyl-methyl taurate | 9 | 8.5 | 8 | 8 | 9 |
| Sodium N-cocoyl glycinate | 0 | 0.6 | 0 | 0 | 0 |
| Sodium N-cocoyl-alanine | 0 | 0 | 1 | 0 | 0 |
| Sodium N-cocoyl-L-glutamate | 0 | 0 | 0 | 1 | 0 |
| Sodium dilauramidoglutamide lysine | 0 | 0 | 0 | 0.1 | 0 |
| Amphoteric surfactant | | | | | |
| Cocamidopropyl betaine | 5 | 6 | 6 | 6 | 6 |
| Sodium cocoamphoacetate | 1 | 0 | 0 | 0 | 1 |
| Cationic polymer | | | | | |
| Cationic guar gum | 0.2 | 0.1 | 0.2 | 0.2 | |
| Cationic locust bean gum | | | | | 0.1 |
| Polyquaternium-10 (Cationic cellulose) | 0.1 | 0.1 | 0.1 | 0.1 | 0.1 |
| Polyquaternium-7 (methyl acrylate/dialkyldimethylammonium chloride | 0.1 | 0 | 0.1 | 0 | 0.1 |
| Propyltrimoniumchloride Acrylamide/Dimethylacrylamide Copolymer | 0 | 0.02 | 0 | 0 | 0 |
| Nonionic surfactant | | | | | |
| Propylene glycol laurate | 0.8 | 0.9 | 0.5 | 1 | 0.8 |
| Diethylene glycol laurate | 0.2 | 0 | 0.3 | 0 | 0.2 |
| Isostearyl alcohol | 0 | 0.1 | 0.2 | 0 | 0 |

-continued

| Test Examples | Formulation example 1 | Formulation example 2 | Formulation example 3 | Formulation example 4 | Formulation example 5 |
|---|---|---|---|---|---|
| Polyoxyethylene hydrogenated castor oil (60E.O.) | 0.1 | 0.1 | 0.2 | 0 | 0.1 |
| Inorganic salt | | | | | |
| Sodium chloride | 1 | 1 | 0.8 | 0.8 | 1 |
| Sodium sulfate | 0 | 0 | 0.2 | 0.2 | 0 |
| Polyhydric alcohol | | | | | |
| Dipropylene glycol | 0.5 | 0 | 0.2 | 0 | 0.5 |
| Glycerin | 0 | 0 | 0.5 | 1 | 0 |
| Propylene glycol | 0 | 0.5 | 0 | 0 | 0 |
| Butylene glycol | 0 | 0 | 0 | 0.5 | 0 |
| Others | | | | | |
| Citric acid | 0.55 | 0.45 | 0.46 | 0.35 | 0.55 |
| L-Arginine | 0.1 | 0 | 0 | 0 | 0.1 |
| L-Glutamic acid | 0.05 | 0 | 0 | 0.1 | 0.05 |
| L-Aspartic acid | 0.05 | 0 | 0 | 0 | 0.05 |
| Camellia oil | 0.01 | 0 | 0.02 | 0 | 0.01 |
| Evening primrose oil | 0 | 0.02 | 0 | 0 | 0 |
| Hydroxyethyl urea | 0.1 | 0 | 0 | 0.1 | 0.1 |
| Lecithin | 0.01 | 0 | 0 | 0 | 0.01 |
| Honey | 0 | 0.1 | 0 | 0 | 0 |
| Hydrolyzed conchiolin | 0 | 0.01 | 0.5 | 0 | 0 |
| Sodium hyaluronate | 0 | 0 | 0.01 | 0 | 0 |
| Sodium benzoate | q.s. | q.s. | q.s. | q.s. | q.s. |
| Phenoxyethanol | q.s. | q.s. | q.s. | q.s. | q.s. |
| EDTA-2Na | q.s. | q.s. | q.s. | q.s. | q.s. |
| Perfume | q.s. | q.s. | q.s. | q.s. | q.s. |

The invention claimed is:

1. A hair cleansing composition, comprising:
   14 to 35% by mass of a sugar, a sugar alcohol, or a mixture thereof;
   5 to 20% by mass of an anionic surfactant;
   wherein at least 50% of said anionic surfactant is the surfactant selected from a group consisting of N-acyl-N-methyl taurate, N-acyl-glutamate, and a mixture thereof;
   5 to 20% by mass of an alkamidopropyl betaine, an alkyl betaine, or a mixture thereof;
   0.05 to 1% by mass of a cationic polymer; and
   0.01 to 1.5% by mass of an inorganic salt;
   wherein the hair cleansing composition has a viscosity in a range of 800 to 20000 mPa·s.

2. The hair cleansing composition, according to claim 1, further comprising:
   a nonionic surfactant comprising a fatty acid residue having 12 to 16 carbon atoms.

3. The hair cleansing composition, according to claim 1, wherein:
   the mass ratio of said anionic surfactant to said alkamidopropyl betaine is in a range of 4/1 to 1/4.

4. The hair cleansing composition, according to claim 1, wherein: said inorganic salt is any salt selected from the group consisting of sodium chloride, sodium sulfate, ammonium chloride, and magnesium chloride.

5. The hair cleansing composition, according to claim 1, wherein:
   said anionic surfactant is 5 to 15% by mass based on said composition.

6. The hair cleansing composition, according to claim 1, wherein:
   said alkamidopropyl betaine, said alkyl betaine, or said mixture thereof is 5 to 15% by mass based on the composition.

7. The hair cleansing composition, according to claim 1, wherein:
   said cationic polymer is a polymer selected from the group consisting of a cationic guar gum, a cationic cellulose, and a quaternary ammonium salt polymer obtained from acrylamide/dimethyldiallylammonium chloride, and the formulation amount of said cationic polymer is in a range of 0.3 to 1% by mass based on said hair cleansing composition.

* * * * *